United States Patent [19]

Katz et al.

[11] Patent Number: 4,888,238

[45] Date of Patent: Dec. 19, 1989

[54] SUPERABSORBENT COATED FIBERS AND METHOD FOR THEIR PREPARATION

[75] Inventors: Leon Katz, Stamford, Conn.; David H. Hollenberg, Neenah, Wis.

[73] Assignee: James River Corporation, Richmond, Va.

[21] Appl. No.: 97,179

[22] Filed: Sep. 16, 1987

[51] Int. Cl.[4] .......................... B05D 3/02; B05D 7/00; D02G 3/00

[52] U.S. Cl. .................................... 428/378; 427/212; 427/389.9; 427/392; 604/371; 604/372; 604/374; 604/375

[58] Field of Search ...................... 427/212, 389.9, 392; 428/378; 604/371, 372, 374, 375

[56] References Cited

U.S. PATENT DOCUMENTS

| | | | |
|---|---|---|---|
| 4,090,013 | 5/1978 | Ganslaw et al. | 525/329.9 |
| 4,128,692 | 12/1978 | Reid | 427/212 X |
| 4,310,593 | 1/1982 | Gross | 428/290 |
| 4,354,487 | 10/1982 | Dozkowski et al. | 428/290 X |
| 4,366,206 | 12/1982 | Tanaka | 428/373 |
| 4,443,492 | 4/1984 | Roller | 427/44 |
| 4,562,114 | 12/1985 | Swanishi et al. | 428/372 |
| 4,600,462 | 7/1986 | Watt | 427/389.9 X |
| 4,605,401 | 8/1986 | Chmelir et al. | 604/368 |

*Primary Examiner*—Michael Lusignan
*Attorney, Agent, or Firm*—Finnegan, Henderson, Farabow, Garrett & Dunner

[57] ABSTRACT

Superabsorbent synthetic fibers are prepared by a method wherein segments of synthetic fibers are coated with a solution of (a) a hydrophilic, uncomplexed polymer and (b) a complexing agent, and the coated fibers are fluff or flash dried causing the polymer to complex and to form a superabsorbent coating on the synthetic fibers in situ.

26 Claims, No Drawings

SUPERABSORBENT COATED FIBERS AND METHOD FOR THEIR PREPARATION

BACKGROUND OF THE INVENTION

The present invention relates to a method of preparing superabsorbent synthetic fibers wherein individual synthetic fibers are coated with a water-soluble polymer which is rendered water insoluble during complexing in situ.

Superabsorbent systems are known in the art. Superabsorbent materials are water insoluble, water swellable compositions of matter which have the capacity to absorb many times their weight in water.

In the prior art known at this time, U.S. Pat. No. 4,090,013 teaches making superabsorbent ionic complexes but does not teach how to coat the resultant polymer onto a substrate. U.S. Pat. No. 4,128,692 discloses precipitating already covalently crosslinked absorbents onto cellulose fibers from an aqueous slurry followed by solvent dehydration. U.S. Pat. No. 4,310,593 teaches the preparation of superabsorbent films and fibers from anionic polyelectrolytes which are crosslinked covalently with an amine/epihalohydrin adduct. The patent also suggests that synthetic and natural fibrous substrates (such as wood pulp) may be coated with said superabsorbent composition.

A need remains, however, to find processes for making superabsorbent fibers that are less complex, less expensive and safer than the processes taught by prior art. The present invention fulfills these needs. Moreover, the process of the present invention has broad application to a large number of synthetic fibers.

Most superabsorbent compositions are sold in powder form for use in products such as absorbent dressings, diapers, tampons, and the like. Superabsorbent particles or powders are difficult to use because they do not remain stationary during the manufacturing process and often change position before the product is completed. Further, superabsorbent powders have the disadvantage of easily absorbing on their extended surface area any water that is present in the production process. The powders will swell and it is very difficult to dry the swelled powders in the finished article. Such articles are thus more difficult and expensive to make because of the additional processing necessary to make them. The difficulty of placing and maintaining the superabsorbent on a substrate has been addressed in many ways: by making webs in which the superabsorbents are placed, by bonding, and by other techniques.

The discrete coated synthetic fibers of the present invention provide an improved solution to these problems. They are easy to use, especially when they are air laid or dry laid in non-woven fabrication processes. The coated fibers can also be mixed with other absorbent materials for use in converted products; one example is as an addition to cellulose fluff pulps for use in diapers. The coated synthetic fibers of the invention can also be incorporated into non-woven card and bind webs or used in melt-blown and other non-woven products, which are typically not hydrophilic, without causing a reduction in strength.

The coated synthetic fibers of the invention are easily used in varying woven and non-woven products, staying more easily in place than absorbent powders and, moreover, have the tremendous range of properties which are related to the particular fiber which forms the base for the superabsorbent polymeric coating. Thus, for example, it is possible to make polyethylene or polypropylene products which are also superabsorbent.

Additional objects and advantages of the invention will be set forth in part in the description which follows, and in part will be apparent from the description, or may be learned by practice of the invention. The objects and advantages of the invention may be realized and attained by means of the instrumentalities and combinations particularly pointed out in the appended claims.

SUMMARY OF THE INVENTION

It has now been found that the above and related objects of the present invention are attained by a method of preparing superabsorbent synthetic fibers coated with a water absorbent polymer that comprises (1) preparing an aqueous solution of an anionic polyelectrolyte and a polyvalent metal salt, said anionic polyelectrolyte being maintained water-soluble in the presence of said polyvalent metal salt by the addition of a neutralizing agent, (2) adding synthetic fibers to the polymeric solution to coat said fibers therewith, and (3) drying said coated synthetic fibers to form a complex of said polyelectrolyte thereon in situ. previously neutral solution becomes acidic causing the anionic polyelectrolytes to complex in situ to form a superabsorbent polymeric coat on each discrete fiber as the fibers are also being dried. The resultant, individual fibers are exceedingly easy to use and quick and inexpensive to make.

Synthetic fibers that can be used include but are not limited to polyester, polyolefin, polyacrylonitrile, polyamide, rayon, cellulose acetate, dacron, and nylon as well as bicomponent fibers. The synthetic fibers are immersed in a solution which is a mixture of a hydrophilic anionic polyelectrolyte and a crosslinking agent. Exemplary of the anionic polyelectrolytes useful in the present invention are the carboxylated, sulfonated or phosphated polymers described in column 3, line 21 to column 4, line 2 of U.S. Pat. No. 4,090,013. The crosslinking or complexing agents are polyvalent metal cations which render the crosslinked polymer substantially insoluble yet highly swellable. The polyvalent metal compounds described in column 4, line 43 to column 5, line 28 of U.S. Pat. No. 4,090,013 are incorporated herein. Preferred metal cation salts include, but are not limited to, aluminum acetate, ammonium zirconium carbonate, chromium acetate, zirconium acetate, aluminum sulfate, aluminum chloride and ferric chloride.

Among the preferred embodiments of the current invention is preparation of a solution wherein polyacrylic acid is mixed with a polyvalent metal salt such as a zirconium or aluminum salt in a ratio of up to 10% by weight of the polymer. The solution has been previously neutralized by addition of an ammonium compound such as ammonium carbonate or ammonium hydroxide or a combination thereof to remain above a pH of 7 so that the polymer and metal ion remain in solution and no complexing occurs. The synthetic fibers are coated with the solution and then flash or fluff dried so that the fibers do not come in contact with one another. Drying vaporizes the ammonia of the neutralizing solution, causing the pH to drop to 7 or less and the polymer to complex in situ on each individual fiber. The coating of the super absorbent fibers can be resolubilized by slurrying the fibers in aqueous solution and raising the pH above 7.

The present invention is a very efficient system for producing discrete superabsorbent synthetic fibers which can be made in a very short time; i.e., in a time that is no longer than wetting and fluff drying the synthetic fibers. Further, the size and configuration of the fibers offers obvious advantages in making non-woven and fluff pulp products.

The advantages of this invention over the prior art include: (1) a method of making synthetic hydrophobic fibers water wettable and absorbent; (2) a method to provide a superabsorbent material that is easily handled and readily incorporated into converted products; (3) a method of coating synthetic fibers in situ which is easily accomplished, causes no viscosity buildup, contains few residual impurities, and is reversible if desired. Further, the crosslinking is achieved simultaneously with the drying of the fibers and without the potentially harmful radiation treatment required by other processes such as are taught in U.S. Pat. No. 4,354,487. Unlike U.S. Pat. No. 4,310,593, and as a further advantage, the preferred ionic complexes are non-toxic.

These and other features and advantages of the present invention will be made more apparent from the following description of the preferred embodiment.

DETAILED DESCRIPTION OF THE PREFERRED EMBODIMENTS

In accordance with a preferred embodiment of the present invention, synthetic fibers are added to an aqueous, neutralized solution of polyacrylic acid containing 1 to 4% by weight of polyvalent metal ions, and the polymeric solution is complexed in situ by means of vaporization of ammonia from the aqueous solution and subsequent fluff or flash drying, causing the polymer to coat the fibrous substrate.

Preferably, the polyacrylic acid solution is first partially neutralized by the addition of a strong alkali such as sodium hydroxide. The extent of neutralization is preferably between 20% and 80% of the available carboxy groups. The extent of the partial neutralization will influence the rate of water absorption of the final superabsorbent product. The solution pH is then adjusted to between 7 and 9, and preferably to between 7.5 and 8, with an ammonium compound, either ammonium carbonate, ammonium hydroxide or a combination thereof. Between 0.5 and 10% by weight of polyvalent metal salt is added thereto. Preferred metal salts include aluminum acetate and ammonium zirconium carbonate.

To the above polymeric solution are added synthetic fibers from ⅛ to ¾ inch long having a denier of 0.9 to 3. The synthetic fibers can be but are not limited to polyester, polyolefin, polyacrylonitrile, polyamide, nylon, dacron, rayon, or cellulose acetate. Once the fibers have been slurried in the aqueous solution, they are fluff dried by suspending the fibers in a stream of hot air, generally from 60° to 100° C. However, heat is not necessary to the fluff drying which can take place at room temperature. The purpose of drying by fluff drying is to draw off the moisture in order to make certain that the dry fibers will be discrete and not matted. The dry fibers are then collected on a screen for use in converted products.

EXAMPLE 1

Superabsorbent solution I was made by the following process. A 25% solids solution of Acrysol A-3 polyacrylic acid (Rohm & Haas) is adjusted to a desired pH of 7.5 to 8 with ammonium carbonate. The necessary amount of ammonium zirconium carbonate (Magnesium Elektron) is added to provide approximately 5% by weight of polyvalent metal salts. A surfactant, such as 0.5% polyethoxy amide, can be optionally added to increase the rate of water absorption. When the metal salt is uniformly incorporated into the solution, ¼ inch rayon fiber is added. After a complete wetting, the fibers are fluff dried at 60° C until dry, causing ammonia to evaporate and the polyacryeic acid to complex on the fiber in situ thus coating the fiber. The increased absorbency of rayon fibers coated by this process can be seen in Table I.

EXAMPLE 2

Sodium hydroxide (6.66 g) was added to a solution of Acrysol A-5 polyacrylic acid (279 g, 8.6% solids) (Rohm & Haas) to provide a 50% neutralized solution. Ammonium carbonate (10 g) was added and the pH was adjusted to 7.5 with ammonium hydroxide. Ammonium zirconium carbonate (15 g of a solution containing 16% solids) was added with stirring. The appropriate fibers were slurried in this solution and then fluff dried as in Example 1. The absorbency of fibers coated with this composition (Superabsorbent 2) is shown in Table 1.

Example 3

Sodium hydroxide (4.24 g) was added to a mixture of Gantrez AN-139 (15 g) poly (methyl vinyl ether/maleic anhydride copolymer) (GAF Corp.) in 60 g of water containing 0.4 g Igepal CA630(GAF Corp.) This provides a 56% neutralized solution. Ammonium carbonate (5 g) was added and the pH was adjusted to 7.5 with ammonium hydroxide. Ammonium zirconium carbonate (15 g of a solution containing 10% solids) was added with stirring. The appropriate fibers were slurried in the solution and then fluff dried as in Example 1. The absorbency of fibers coated with this composition (Superabsorbent 3) is shown in Table 1.

TABLE I

| | SUPERABSORBENTS ON FLUFF DRIED SYNTHETIC FIBERS | |
|---|---|---|
| SAMPLE | ABSORPTION (g $H_2O$/g SUBSTRATE) | ABSORPTION (g $H_2O$/g SUPERABSORBENT) |
| ¼" RAYON | | |
| - Control | 12.6 | — |
| 10% Superabsorbent 1 | 28.7 | 174 |
| 10% Superabsorbent 1 + 0.5% Polyethoxy amine | 34.8 | 235 |
| 10% Superabsorbent 2 | 69 | 577 |
| 10% Superabsorbent 3 | 51 | 397 |
| ¾" POLYACRYLONITRILE | | |
| - Control | 16.9 | — |
| 10% Superabsorbent 2 | 21.8 | 66 |
| ¼" POLYESTER | | |
| - Control | 9.4 | — |
| 10% Superabsorbent 2 | 51.8 | 433 |
| 10% Superabsorbent 3 | 22.3 | 138 |
| PULPEX E-338 | | |
| - Control | — | — |
| 10% Superabsorbent 1 | 52.2 | 522 |
| 10% Superabsorbent 1 | 67 | 337 |
| 30% Superabsorbent 1 | 106 | 354 |

Other embodiments of the invention will be apparent to one skilled in the art from a consideration of the specification, especially Table 1, or with the practice of the disclosed invention. It is intended that the specification and specific examples be considered as exemplary only with the true scope and spirit of the invention being indicated by the claims.

What is claimed is:

1. A method of preparing superabsorbent synthetic fibers coated with a water absorbent polymer which comprises (1) preparing an aqueous solution of an anionic polyelectrolyte and a polyvalent metal salt, said anionic polyelectrolyte being maintained water-soluble in the presence of said polyvalent metal salt by the addition of a neutralizing agent, (2) adding synthetic fibers to the polymeric solution to coat said fibers therewith, and (3) fluff drying said coated synthetic fibers to form a complex of said polyelectrolyte thereon in situ.

2. The method of claim 1 wherein said anionic polyelectrolyte is polyacrylic acid or poly (methyl vinyl ether/maleic anhydride copolymer).

3. The method of claim 1 wherein said polyvalent metal salt is selected from aluminum acetate, ammonium zirconium carbonate, chromium acetate, zirconium acetate, aluminum acetate, aluminum chloride and ferric chloride.

4. The method of claim 1 wherein said polyvalent metal salt is aluminum acetate or ammonium zirconium carbonate.

5. The method of claim 1 wherein said polyvalent metal salt is present in solution in an amount of 0.5 to 10% by weight.

6. The method of claim 1 wherein the synthetic fibers are cellulose acetate, polyester, polyolefin, polyacrylonitrile, polyamide, dacron, nylon or a bicomponent fiber.

7. The method of claim 1 wherein the polyelectrolyte solution is maintained at a pH between 7 and 9 by the addition of ammonium carbonate, ammonium hydroxide or a mixture thereof to the solution.

8. The method of claim 6 wherein the polyelectrolyte solution is maintained at a pH between 7.5 and 8.

9. The method of claim 1 wherein the fibers are dried by suspending the fibers in a stream of hot air at a temperature between 60° and 100° C.

10. The method of claim 7, wherein the fibers are dried in a stream of air at room temperature.

11. The method of claim 1 wherein the synthetic fibers have a denier of 0.9 to 3.

12. The method of claim 1 wherein the synthetic fibers have a length of $\frac{1}{8}$ to $\frac{3}{4}$ inches.

13. A coated fiber produced by the method of claim 12.

14. A coated fiber produced by the method of claim 11.

15. A coated fiber produced by the method of claim 10.

16. A coated fiber produced by the method of claim 9.

17. A coated fiber produced by the method of claim 8.

18. A coated fiber produced by the method of claim 7.

19. A coated fiber produced by the method of claim 6.

20. A coated fiber produced by the method of claim 5.

21. A coated fiber produced by the method of claim 4.

22. A coated fiber produced by the method of claim 3.

23. A coated fiber produced by the method of claim 2.

24. A superabsorbent material consisting of a synthetic fiber coated with a substantially dry water-absorbent polymer which comprises a hydrophilic polymer crosslinked with a polyvalent metal salt.

25. A superabsorbent material according to claim 24 wherein the synthetic fiber is cellulose acetate, polyester, polyolefin, polyacrylonitrile, polyamide, dacron, nylon, rayon, or a bicomponent fiber.

26. A superabsorbent material according to claim 24 wherein the hydrophilic polymer is an anionic polyelectrolyte selected from polyacrylic acid and poly (methyl vinyl ether/maleic anhydride copolymer) and is crosslinked in situ with a polyvalent metal salt selected from aluminum acetate, ammonium zirconium carbonate, chromium acetate, zirconium acetate, aluminum acetate, aluminum chloride and ferric chloride.

* * * * *